United States Patent [19]

Cooper

[11] Patent Number: 4,983,329
[45] Date of Patent: Jan. 8, 1991

[54] PREPARATION OF ESTERIFIED PROPOXYLATED GYLCERIN FROM FREE FATTY ACDIDS

[75] Inventor: Charles F. Cooper, Paoli, Pa.

[73] Assignee: Arco Chemical Technology, Inc., Wilmington, Del.

[21] Appl. No.: 384,142

[22] Filed: Jul. 27, 1989

Related U.S. Application Data

[63] Continuation-in-part of Ser. No. 237,018, Aug. 26, 1988, abandoned.

[51] Int. Cl.$^5$ ................................................ C11C 3/02
[52] U.S. Cl. .............................. 260/410.7; 260/410.6; 426/611
[58] Field of Search .......................... 260/410.6, 410.7; 426/611

[56] References Cited

U.S. PATENT DOCUMENTS 3,337,595  8/1967  Lamont ........................... 260/410.6
4,600,539  7/1986  Hoppe et al. ..................... 260/410.7

Primary Examiner—Werren B. Lone
Assistant Examiner—Vera C. Clarke
Attorney, Agent, or Firm—Delbert E. McCaslin

[57] ABSTRACT

A novel method is provided for the preparation of a esterified propoxylated glycerin having food grade quality by reacting at temperatures of from about 100° C. to about 250° C. a propoxylated glycerin having from 2 to 100 oxypropylene oxide units per glycerin with excess C10–C24 fatty acids and purifying the reactant product by methanol extraction or steam stripping and neutralization of excess fatty acid.

14 Claims, No Drawings

PREPARATION OF ESTERIFIED PROPOXYLATED GYLCERIN FROM FREE FATTY ACDIDS

CROSS REFERENCE TO RELATED APPLICATIONS

This application is a continuation-in-part application of allowed co-pending application Ser. No. 07/237,018, filed Aug. 26, 1988, and entitled Preparation Of Esterified Propoxylated Glycerin From Free Fatty Acids, now abandoned.

FIELD OF THE INVENTION

This invention relates to the preparation of esterified propoxylated glycerin from free fatty (C10–C24) acids which are particularly useful as non-caloric food substitutes for edible fats and oils and thus have an acceptable food grade quality.

BACKGROUND OF THE INVENTION

Edible, wholly or partially non-digestible low calorie fat materials and methods for the preparation thereof are known. Much has been written about the adverse health problems of high fat diets, thus indicating clearly an interest in and a need for a fat substitute that is either entirely non-digestible, or has a reduced caloric value. The recent interest in non-caloric food substitutes has resulted in several classes of compounds being proposed. One suggested class has been esterified propoxylated glycerins. However, because the recommended methods of preparation either required toxic catalysts which cannot be completely removed or result in a product with unacceptable acidity, new process methods are needed. The instant invention overcomes these problems and is directed to a novel method for preparing esterified propoxylated glycerin with a food grade quality.

European Patent No. 254,547 discloses that esterified propoxylated glycerins can be used as non-caloric food substitutes. References cited therein provide a good review of the field relating to fat substitutes, methods for their preparation and problems associated therewith. Two methods of preparation are described in EP 254,547 none of which can be used to prepare a food grade product. The preferred method is to react fatty acids with a propoxylated glycerin using p-toluenesulfonic acid as catalyst allowing catalyst residues at unacceptable levels even after purification. The same was observed using the metal catalysts exemplified hereinafter. An alternative method, with is exemplified in the examples of EP No. 254,547 reacts the propoxylated glycerin with a fatty acid chloride in the presence of a tertiary amine such as pyridine. Not only would such methods be technically impractical for commercialization but would require column chromatography for any purification. Food grade products must be essentially catalyst free unless the catalyst is by itself non-toxic. This is not true for sulfonic acids or most of the Lewis acid metals which may be utilized as catalysts. None of the methods described in EP 254,547 could be acceptable as food grade products.

U.S. Pat. No. 3,337,595 describes a method for preparing fatty esters of propoxylated glycerins where the propoxylated glycerin has a molecular weight above 600. These esters are disclosed as being useful for controlling, suppressing and/or preventing foaming of aqueous systems having foaming tendencies in industrial processes. The process is not suitable for preparing food grade products. The acid values (maximum of 25 KOH/g) are much too high for an edible oil. Only stoichiometric quantities of reactants are employed resulting in a method too slow to be considered for a practical commercial process.

SUMMARY OF THE INVENTION

According to the present invention there is provided an improved method for the preparation of a food grade esterified propoxylated glycerin by direct esterification with excess free fatty C10 to C24 acid such as oleic acid and the removal of most of the excess fatty acid by extraction with methanol or vacuum steam stripping and neutralization of any remaining acid.

It is an object of this invention to provide a novel method for the preparation of esterified propoxylated glycerin having food grade quality by direct esterification of a propoxylated glycerin with an excess of a C10 to C24 saturated or unsaturated fatty acid or mixtures thereof.

A particular advantage of the method of the instant invention as compared to prior art methods is that esterification of the propoxylated glycerin can be carried out directly prior to the removal of any propoxylation (alkali metal alkoxylate) catalyst.

These and other objects and advantages of this invention will become apparent from the description of the invention and from the claims.

DETAILED DESCRIPTION OF THE INVENTION

In accordance with the present invention, esterified propoxylated glycerins are prepared by reacting at temperatures of from about 100° C. to about 250° C. preferably from 150° C. to 225° C. a propoxylated glycerin having from 2 to 100, preferably from 5 to 25, oxypropylene oxide units per glycerin and having a molecular weight range of from about 200 to about 5900, with an excess of a saturated or unsaturated C10 to C24 fatty acid or mixtures thereof, such as, for example, mixed soya fatty acids, and thereafter removing excess unreacted fatty acid by a wash extraction with methanol or by vacuum steam distillation (stripping) at temperatures of from about 180° C. to about 220° C. followed by alkali (potassium or sodium hydroxide) neutralization and filtration and optionally adsorption, precipitation with $CO_2$ or ion exchange. Decolorization of the esterified product if required can be achieved by heating with activated charcoal or bleaching earths.

The esterification rate of the propoxylated glycerin can be enhanced by carrying out the reaction under reduced pressures of from about 0.01 mm up to atmospheric and preferably from about 1 mm to about 50 mm mercury, with gas or low boiling liquid stripping or a combination of both.

In order to produce an esterified propoxylated glycerin having food grade quality, the acidity of the product must be lowered to an acceptable level. As indicated hereinabove this is accomplished according to a method of the present invention by vacuum steam stripping or by extraction of the acid with methanol. Extraction with methanol forms a two phase system with the top phase containing the methanol and extracted acid and the bottom phase containing the esterified propoxylated glycerin and small amounts of the acid reactant. The extraction procedure may be repeated as many times as desired with fresh methanol. Following the steam stripping or extraction procedure neutralization may be essentially effected with the addition of an alkali metal hydroxide such as KOH OR NaOH. Without the initial lowering of the acidity level as described, the final acceptable acidity of the product for food grade quality can only be achieved with difficult procedures and loss of product. A particular advantage of employing methanol extraction is that it is a low temperature process which can be carried out at temperatures of from about $-10°$ C. to about 50° C., and problems of low level decomposition do not become a processing problem. In addition, all of the acid rich extracts as well as the methanol may be recycled.

Propoxylation of glycerin can be carried out by the addition of propylene oxide to glycerin in the presence of a catalytic amount of an alkali metal alkoxylate at temperatures of from about 70° C. to about 130° C. preferably 90° C. to 110° C. and the propylene oxide added at the autogenous pressures of the reaction system and generally at a rate to maintain a pressure in the reactor of about 50 to 60 psi. The alkali metal alkoxylate can generally be prepared by heating at temperatures of from about 100° C. to 110° C. KOH or NaOH with glycerin while continuously removing water, preferably under reduced pressure and is employed in the propoxylation reaction in a range of from about 0.0003 mol to about 3.3 mol preferably from 0.003 to 1.0 mol of alkali metal content per 100 g. glycerin employed. The degree of propoxylation is controlled and thus the molecular weight, by regulating the amount of propylene oxide fed into the reactor. After the desired molecular weight is reached, the potassium or sodium is normally removed by any suitable method such as adsorption, ion exchange, or extraction.

The C10 to C24 fatty acids which may be employed as reactants in the present invention may be saturated or unsaturated fatty acids or mixtures thereof. As indicated hereinabove an excess of the fatty acid is employed in the reaction system in order to have the esterification reaction proceed adequately without the addition of other catalysts. Illustrative of such C10 to C24 fatty acids which may be employed include, for example, the saturated acids such as capric, lauric, myristic, pentadecanoic, n-hexadecanoic (palmitic), heptadecanoic, stearic, nonadecanoic n-eicosanoic, n-docosanoic and n-tetracosanoic. The unsaturated acid which may be employed include dodecylenic, palmitoleic, oleic, linoleic, linolenic, eicsenoic, arachidonic, docosahexaenoic and selacholeic. As indicated hereinabove, mixtures of acids either saturated or unsaturated or mixtures of both may be employed. Soya fatty acids which contain predominately palmitic (9.8%), stearic (2.4%), oleic (28.9%), linoleic (50.7%) and linolenic (6.5%) along with minor amounts of lauric, myristic, arachidoc, palmitoleic and monoethanoic acids may be employed in the method of the present invention.

As indicated, a particular advantage of the instant invention is that the esterification employing excess fatty acid can be carried out directly with the propoxylated glycerin after formation thereof and prior to the removal of the alkali metal catalyst employed to prepare same. The propoxylated glycerin may of course be treated to remove the alkali metal catalyst, e.g. potassium. However, such treatment and removal thereof, which is generally with large volumes of magnesium silicate with lower molecular weight materials, is difficult and costly.

The reactive steps of the present invention i.e., propoxylation, esterification and purification may be carried out in any suitable reactor which is generally equipped with a means for agitation and a means for regulating temperature and pressure. The reaction may be carried out as a batch or continuous process.

The instant invention is more fully illustrated by the following examples, which include particular features of the invention as well as comparative results. However, the examples are not to be construed as limiting the invention in any way, it being understood that numerous variations are possible without departing from the spirit and scope of the invention. All parts are in parts by weight unless otherwise indicated.

EXAMPLE 1

PROPOXYLATION OF GLYCERIN 992 parts of glycerin was heated with 25 parts of 85% potassium hydroxide (KOH) solution at 100° C. and 10 mm pressure in a stainless steel stirred autoclave with a dry ice trap for water removal until no further water was being evolved. The reactor was pressurized with nitrogen and cooled to 92° C. and 5170 parts of propylene oxide added on a pressure demand basis maintaining a reactor pressure of 55 psi. After the propylene oxide had been added the reaction was continued for an additional 5 hours. The reactor was then cooled and purged with nitrogen to provide a propoxylated glycerin for esterification. Potassium was essentially removed from the propoxylated glycerin by heating to 90° C. for 2 hrs. with 600 g. of magnesium silicate and 60 g water to give a 290–310 mg KOH/g hydroxyl number.

EXAMPLES 2-12

ESTERIFICATION OF PROPOXYLATED GLYCERIN 556 parts (1 mol) of propoxylated glycerin of Example 1 was heated with oleic acid at various temperatures, pressures, time and amount, if any, of an excess of fatty acid over stoichiometric quantity in a three neck reaction flask equipped with a thermometer and a distilling head (Dean-Stark). Overhead acid was recycled back to the reaction flask. The reaction was stopped when the acidity-corrected hydroxyl number was less than 5 mg KOG/g. The conditions and results are set forth in Table 1 below showing % conversion (OH). Examples 3, 5 and 6 were carried out with stoiciometric amounts of oleic acid.

TABLE 1

| Ex. No. | Time (Hrs.) | Temp. °C. | Pressure | Oleic Acid (Mol % Excess) | Conversion (% OH) |
|---|---|---|---|---|---|
| 2 | 20 | 200 | 1 atm. | 20 | 96 |
| 3 | 36 | 200 | 10 torr | 0 | 95 |
| 4 | 8 | 200 | 10 torr | 20 | 95 |
| 5 | 96 | 200 | 1 atm. | 0 | 94 |
| 6 | 17 | 250 | 1 atm. | 0 | 96 |
| 7 | 7 | 250 | 1 atm. | 20 | 95 |
| 8 | 11 | 250 | 1 atm. | 20 | 99 |
| 9 | 4 | 250 | 10 torr | 20 | 94 |
| 10 | 15 | 200 | 1 atm. | 50 | 95 |
| 11 | 10 | 200 | 1 atm. | 50 | 96 |
| 12 | 5 | 200 | 10 torr | 50 | 95 |

EXAMPLES 13-18

A number of runs were made according to the procedure of Examples 2-12 using oleic acid but with different molecular weight propoxylated glycerin. In Examples 13-17 a propoxylated glycerin of 382 molecular weight was employed along with a 20 mol % excess of oleic acid. In Example 18 the molecular weight of the propoxylated glycerin was 904 (14 oxypropylene oxide units per glycerin) which was employed with stoichiometric oleic acid. The results and conditions are set forth in Table 2.

TABLE 2

| Ex. No. | Time (Hrs.) | Temp. °C. | Pressure | Conversion (% OH) |
|---|---|---|---|---|
| 13 | 96 | 170 | 1 atm. | 94 |
| 14 | 144 | 170 | 1 atm. | 97 |
| 15 | 24 | 170 | 10 torr | 95 |
| 16 | 23 | 200 | 1 atm. | 94 |
| 17 | 8 | 200 | 10 torr | 96 |
| 18 | 168 | 200 | 1 atm. | 94 |

EXAMPLES 19-26

The procedure of Examples 2-12 was repeated using stoichiometric amounts of fatty acid but including the traditional p-toluene sulfonic acid (PTSA) and methansulfonic acid (MSA) as catalyst. Catalyst was removed by washing with an equal volume of water and/or 10% NaOH wash. In Examples 19-24, 846 parts of oleic acid or 852 parts of stearic acid (Examples 25-26) with 556 parts (1 mol) of propoxylated glycerin was employed in the reaction. When employing the traditional sulfonic acid catalysts it is important that sulfur levels of the esterified product be very low, i.e. on the order of less than 1 ppm. Results and conditions are set forth in Table 3 below.

TABLE 3

| Ex. No. | Catalyst (wt %) | Temp °C. | Removal Method | Sulphur PPM | Catalyst Removal (%) |
|---|---|---|---|---|---|
| 19 | PTSA (2.0) | 110 | A | 3500 | — |
| 20 | PTSA (2.0) | 110 | B | 370 | 89 |
| 21 | PTSA (2.0) | 110 | C | 360 | 90 |
| 22 | MSA (0.46) | 150 | A | 1200 | — |
| 23 | MSA (0.46) | 150 | B | 360 | 70 |
| 24 | MSA (0.46) | 150 | C | 350 | 71 |
| 25 | PTSA (0.52) | 150 | B | 270 | 72 |
| 26 | PTSA (0.52) | 150 | C | 260 | 73 |

A: No Treatment
B: Water Wash (equal volume; 5x)
C: Water wash (equal volume; 5x) followed by 10% NaOH wash (equal volume; 1x)

EXAMPLES 27-36

The procedure of Examples 19-26 was repeated using stoichiometric amounts of oleic acid but employing metal Lewis Acid catalysts at a reaction temperature of 150° C. Catalyst was removed by washing with an equal volume of water and/or 10% NaOH of water. The effectiveness of adsorption of the catalyst (metal) was tested by heating the product to 90° C. for 2 hours with 5% by weight magnesium silicate and filtering. Catalyst residue levels were determined by X-ray analysis. The results are set forth in Table 4 below.

TABLE 4

| Ex. No. | Catalyst (wt. % conc) | Treatment Method | Metal Conc. (PPM) |
|---|---|---|---|
| 27 | $SnCl_2$(0.6) | A | 3800 |
| 28 | $SnCl_2$(0.6) | B | 100 |
| 29 | $SnCl_2$(0.6) | A | 162 |
| 30 | $SnCl_2$(0.6)) | B | 23 |
| 31 | $SnCl_2$(0.6) | C | 29 |
| 32 | $SnCl_2$(0.6) | D | 12 |
| 33 | Ti(O—Pr)$_4$*(0.68) | A | 2400 |
| 34 | Ti(O—Pr)$_4$(0.68) | B | 630 |
| 35 | Ti(O—Pr)$_4$(0.68) | C | 560 |
| 36 | Ti(O—Pr)$_4$(0.68) | D | 340 |

*Ti(O—Pr)$_4$ - titanium isopropoxide
A: No Treatment
B: Magnesium Silicant (5%, 90° C., 2 hrs)
C: Water wash (equal volume, 5x)
D: Water wash (equal volume, 5x); magnesium silicate (5%, 90° C., 2 hrs)

EXAMPLE 37

ACIDITY REDUCTION—VACUUM STEAM DISTILLATION

The product of Example 2 was heated to between 200°-205° C. under 10 mm pressure and water slowly bled beneath the surface of the liquid. Total amount of water added was 3 parts water (190 grams) per part esterified propoxylated glycerin product. The acidity was decreased from 0.588 meq/g (33 mg KOH/g) to less than 0.04 meq/g (1.9 mg KOH/g).

EXAMPLES 38-42

ACIDITY REDUCTION—METHANOL EXTRACTION

A number of runs were carried out using the reaction products from Examples 4,7,8,9 and 10 containing excess oleic acid. Samples of the reaction products were mixed with specified volumes of methanol and agitated. The biphasic mixture was allowed to separate and the procedure optionally repeated with fresh methanol. The methanol to product volume of Examples 38 and 39 was 1:1, with Examples 40 and 41 being 2:1. Example 42 was a continuous extraction at 5:1 (v/v) MeOH/product. The results are shown in Table 5.

TABLE 5

| Example No. | Extractions No. | Initial Acid Level (mg KOH/g) | Final Acid (mg KOH/g) | % Acid Reduction | % Ester Recovered |
|---|---|---|---|---|---|
| 38 | 1 | 36 | 23 | 36 | 97 |
| 39 | 5 | 36 | 7 | 80 | 89 |
| 40 | 1 | 35 | 6 | 83 | 87 |
| 41 | 5 | 35 | 0.8 | 98 | 80 |
| 42 | — | 34 | 6 | 82 | 81 |

EXAMPLE 43

NEUTRALIZATION OF EXCESS ACID 100 parts of the product from Example 38 subjected to methanol extraction was mixed with 0.4 parts of 50% KOH and stirred for 1 hour. The precipitated fatty acid salts were filtered and the product heated with magnesium silicate for 2 hours at 90° C. and filtered. The final acidity was 0.4 mg KOH/g (compared to 0.3 mg KOH/g for an available commercial edible oil) and the potassium level was 5 ppm.

EXAMPLE 44

4437 grams of mixed soya fatty acids were heated at 200° C. with a nitrogen purge to remove water with 3000 grams of 556 molecular weight propoxylated glycerin from which the propoxylation catalyst had been removed. After the hydroxyl content had dropped to less than 6 mg KOH/g, the mixture was cooled and enough saturated NaOH added to precipitate the acid as the sodium salt. The mixture was filtered to yield 6567 grams of mixed soya fatty ester of propoxylated glycerin.

EXAMPLE 45

55 grams of 550 molecular weight propoxylated glycerin containing 0.04 meq/g propoxylated glycerin alkoxylate catalyst (0.25 wt. % potassium) was mixed with 110 grams of mixed soya fatty acids in a 500 ml bottom flask equipped with a thermometer, condenser with a Dean-Stark trap and stirrer. The reaction mixture was heated to 225° C. with a nitrogen purge for 12 hours and then cooled and the potassium salt removed by filtration. The mixture was steam stripped under 10 mm pressure until the acidity was 1 mg KOH/g and cooled. 0.5 grams of 50% NaOH was added and the product filtered. The final acidity was 0.1 mg KOH/g with a hydroxyl number of 1.5 mg KOH/g (99% hydroxyl conversion).

EXAMPLE 46

4285 grams of stearic acid was mixed with 3000 grams of 556 molecular weight propoxylated glycerin, from which the propoxylation catalyst had been removed, at 200° C. with a nitrogen purge to remove water. After the hydroxyl content had dropped to less than 6 mg KOH/g the mixture was cooled to give a white solid esterified product.

EXAMPLE 47

55 grams of 550 molecular wight propoxylated glycerin containing 0.2 meq/g propoxylated glycerin alkoxylate catalyst (0.8 wt. % potassium) was mixed with 106 grams of oleic acid as in the procedure of Example 45. The reaction mixture was heated to 200°–235° C. with a nitrogen purge for 12 hours, cooled and diluted with hexane. After filtration, the hexane was removed under vacuum and the product analyzed. Acidity was 0.3 mg KOH/g and the hydroxyl number was 1.4 mg KOH/g representing greater than 99% conversion.

EXAMPLE 48

The procedure of Example 47 was repeated employing 550 MW propoxylated glycerin containing 0.04 meq/g propoxylated glycerin alkoxylate (0.25 wt. % potassium). The mixture was heated to 225° C. with a nitrogen purge for 12 hours cooled and the potassium salt removed by filtration. The mixture was steam stripped under 10 mm pressure until the acidity was 2 mg KOH/g and cooled. 0.04 grams of 50% NaOH was added and the product filtered. The acidity was 0.1 mg KOH/g and the hydroxyl number 1.0 mg KOH/g (99% hydroxyl conversion).

EXAMPLE 49

55 grams of 550 MW propoxylated glycerin containing 0.04 meq/g propoxylated glycerin alkoxylate catalyst (0.25 wt. % potassium) was mixed with 107 grams of stearic acid in a 500 ml round bottom flask equipped with a thermometer, condenser with a Dean-Stark trap and stirrer. The mixture was heated to 200° C. with a nitrogen purge for 15 hours, cooled to 30° C. and the potassium salt removed by filtration. The mixture was steam stripped under 10 mm pressure until the acidity was 5 mg KOH/g and cooled. 0.5 grams of 50% NaOH was added at 30° C. and the product filtered. After cooling the product was a waxy solid with an acidity of 0.1 mg KOH/g and a hydroxyl number of 1.0 mg KOH/g (99% hydroxyl conversion).

EXAMPLE 50

PROPOXYLATION OF GLYCERIN (LOWER PRESSURES)

992 parts of glycerin was heated with 25 parts of 85% KOH at 110° C. and 10 mm pressure until no further water was being evolved. The reactor was cooled to 92° C. and 5170 parts of propylene oxide added at such a rate that a pressure of 25 psi was maintained. After the propylene oxide had been added the reaction was continued for 5 hrs. longer. The reaction was cooled and purged with nitrogen, and the product heated with 600 grams magnesium silicate and 60 grams water for 2 hours at 90° C. Hydroxyl number was 303 mg KOH/g.

I claim:

1. A method for the preparation of an esterified propoxylated glycerin which comprises the steps of:
   propoxylating glycerin at a temperature of from about 70° C. to about 130° C. with propylene oxide, added at the autogenous pressure of the reaction system, in the presence of from about 0.0003 mol to about 3.3 mol of alkali metal content of an alkali metal alkoxylate catalyst per 100 g glycerin employed to give a propoxylated glycerin having from 2 to 100 oxypropylene oxide units per glycerin;
   esterifying the propoxylated glycerin directly, without the removal of alkali metal propoxylated glycerin catalyst, at a temperature of from about 100° C. to about 250° C. with an excess of a saturated or unsaturated C10 to C24 fatty acid or mixtures thereof to provide an esterified propoxylated glycerin product; and
   purifying the esterified propoxylated glycerin product by a wash extraction with methanol at temperatures of from about −10° C. to about 50° C., or vacuum steam stripping at temperatures of from about 180° C. to about 220° C. to remove excess unreacted fatty acid, followed by neutralization with an alkali metal hydroxide and filtering to essentially remove and reduce alkali metal content and to provide a food grade esterified propoxylated glycerin.

2. A method according to claim 1 wherein the propoxylation catalyst is employed in an amount of from 0.003 mol to 1.0 mol based on alkali metal content.

3. A method according to claim 1 wherein the esterification is carried out under a reduced pressure of from about 0.01 mm up to about atmospheric.

4. A method according to claim 3 wherein the pressure is from 1 mm to 50 mm of mercury.

5. A method according to claim 1 wherein the propoxylation is carried out at temperatures of from 90° C. to 110° C.

6. A method according to claim 1 wherein the propoxylated glycerin has from 5 to 25 oxypropylene oxide units per glycerin.

7. A method according to claim 1 wherein the esterification is carried out at temperatures of from 150° C. to 225° C.

8. A method according to claim 1 wherein the alkali metal of the alkoxylate catalyst is potassium.

9. A method according to claim 1 wherein the fatty acid is selected from the group consisting of oleic, stearic and mixed soya fatty acids.

10. A method according to claim 9 wherein the fatty acid is oleic acid.

11. A method according to claim 1 wherein the neutralization is with sodium or potassium hydroxide.

12. A method according to claim 1 wherein the esterified propoxylated glycerin product is decolorized.

13. A method according to claim 1 wherein the alkoxylate catalyst is essentially removed prior to esterifying the propoxylated glycerin.

14. A method according to claim 1 wherein the rate of addition of propylene oxide is at a rate to maintain a pressure in the reactor of from about 50 to about 60 psi.

* * * * *

UNITED STATES PATENT AND TRADEMARK OFFICE
CERTIFICATE OF CORRECTION

PATENT NO. : 4,983,329

DATED : January 8, 1991

INVENTOR(S) : Charles F. Cooper

It is certified that error appears in the above—identified patent and that said Letters Patent is hereby corrected as shown below:

ON TITLE PAGE: Item [54], Column 1, lines 2 & 3

Second Line Of Title Change "GYLCERIN" to --GLYCERIN--

Last Line Of Title Change "ACDIDS" to --ACIDS--

Signed and Sealed this

Twenty-eighth Day of April, 1992

Attest:

HARRY F. MANBECK, JR.

Attesting Officer

Commissioner of Patents and Trademarks